United States Patent [19]

Shibata et al.

[11] 4,138,496
[45] Feb. 6, 1979

[54] SY-1 SUBSTANCE

[75] Inventors: Akira Shibata, Zama; Yukio Miyazaki, Ageo; Kiyoshi Tsuda, Tokyo; Noboru Otake, Yokohama; Haruyasu Kinashi, Tokyo, all of Japan

[73] Assignee: Kaken Chemical Co., Ltd., Tokyo, Japan

[21] Appl. No.: 808,611

[22] Filed: Jun. 21, 1977

[51] Int. Cl.² .................... A61K 31/35; C07D 309/06
[52] U.S. Cl. ................. 424/283; 260/345.7 R; 260/345.8 R
[58] Field of Search ................. 260/345.7 R, 345.8 R; 424/283

[56] References Cited
FOREIGN PATENT DOCUMENTS
5186191 7/1976 Japan ................................ 260/345.7

OTHER PUBLICATIONS
Miyazaki et al., Chem. Abstract, 85, 172209w (1976).

Primary Examiner—Nicky Chan
Attorney, Agent, or Firm—Oblon, Fisher, Spivak, McClelland & Maier

[57] ABSTRACT

SY-1 substance has the following formula:

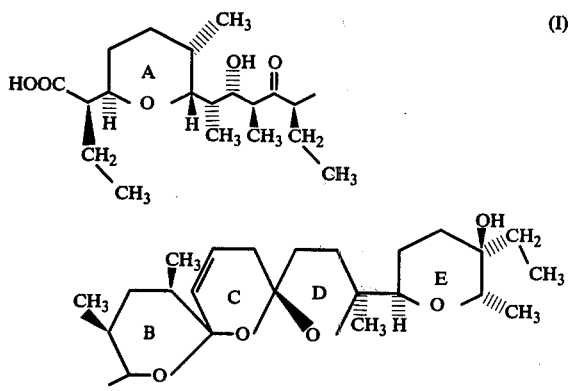

The SY-1 substance and esters and salts thereof are antibiotics which have antibacterial, antifungal, antiviral and anticoccidial activity and also increase feed-utilization efficiency in ruminants.

4 Claims, No Drawings

SY-1 SUBSTANCE

BACKGROUND OF THE INVENTION

1. Field of the Invention

This invention relates to SY-1 substance and esters and salts thereof.

2. Disclosure of the Prior Art

Antibiotic SY-1 substance is a new member of polyether antibiotics. Especially, it resembles Salinomycin in chemical structure.

The inventors of this application have reported that SY-1 substance is produced by fermentation of Salinomycin producing strain belonging to Streptomyces in (Japan-Kokai 76-86191 published on July 28, 1976).

SUMMARY OF THE INVENTION

One object of this invention is to provide SY-1 substance and esters and salts thereof.

Another object of this invention is to provide a new production process of SY-1 substance and esters and salts thereof.

The SY-1 substance and esters and salts thereof have antibacterial, antifungal, antiviral and anticoccidal activity, and also increase feed-utilization efficiency in ruminants.

DETAILED DESCRIPTION OF THE INVENTION

SY-1 substance has the following formula:

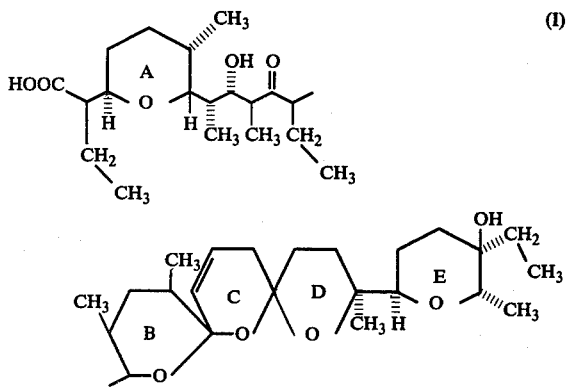

SY-1 substance can also occur in the form of pharmaceutically acceptable salts and esters particularly the sodium, potassium and calcium salts and lower alkyl esters such as methyl, ethyl, propyl and butyl esters.

SY-1 substance can be produced by submerged aerobic fermentation of Streptomyces albus in the manner usually used for Actinomycetes culture, and extracted from at least one of the mycelial mass and the filtered broth. SY-1 substance is preferably produced by fermentation of Streptomyces albus 80614 (ATCC21838, FERM-P 419) or its mutants.

SY-1 substance can be produced by the processes commonly employed for culturing Actinomycetes. For industrial scale production, however, submerged aerobic fermentation is preferred. Culture temperature is preferably from 25° C. to 30° C. The culture medium can be one usually used for culturing Actinomycetes, which comprises carbon sources, nitrogen sources, inorganic salts, a small amount of organic substances and antiforming agent. Maximum production of SY-1 substance usually occurs after 72-120 hours from the start of fermentation.

SY-1 substance can be isolated by utilizing its physicochemical properties. SY-1 substance is soluble in various organic solvents and accordingly, it can be isolated by a solvent extraction process. Because SY-1 substance exists in both of mycerial mass and the filtered broth, a suitable amount of an organic solvent, such as ethyl acetate, butyl acetate, n-hexane or chloroform, is preferably added to the whole fermentation broth with stirring, so that the strain is autolyzed and SY-1 substance in the strain is readily extracted by the organic solvent.

The solvent phase is separated from the aqueous and solid phases, concentrated under vacuum and purified by column chromatography on almina or the like. Preferred solution for development is ethyl acetate, benzene, n-hexane, methanol, acetone or a mixture thereof. It is preferable to use a mixture of ethyl acetate and methanol at a ratio of 100 : 1 to 3. The eluate is fractionated and each fraction is checked by thin layer chromatography to identify the spot of SY-1 substance. The fractions showing single spot of SY-1 substance were combined, concentrated under vacuum and chilled at -5° C. to crystallize SY-1 substance.

Coproduced salinomycin is separated from SY-1 substance by chromatography on almina.

Crude crystalline SY-1 substance is then separated by filtration. The cyrstal is dissolved in the solvent such as ethyl acetate, hexane and benzene, concentrated under vacuum, and chilled for crystallization to occur. The recrystallization is repeated to give more purified cyrstalline SY-1 substance.

Physicochemical and biological properties of SY-1 substance (Na salt) are as follows:

| | |
|---|---|
| (1) | $Mp_{\cdot}$ 120–122° C |
| (2) | $[\alpha]_D^{25} = -13°$ C (C = 1, MeOH) |
| (3) | Solubility: soluble in alcohols, acetates, chloroform, ether, carbon tetrachloride, benzene and n-hexane; insoluble in water. |
| (4) | Stability: stable in pH 7–9; unstable in pH lower than 6. |
| (5) | Color reaction: negative for Lemieux reaction, ninhydrin reaction, ferric chloride reaction, vanillin reaction and Fehling's reaction; positive for iodine reaction to show reddish brown. |
| (6) | Elemental analysis: C:66.35; H:9.19; O:21.42 |
| (7) | Molecular formula: $C_{42}H_{69}O_{10}Na$ |
| (8) | Molecular weight: 756 ($M^+$ m/e) |
| (9) | UV spectrum: $\lambda_{max}^{MeOH} = 285$ nm ($\epsilon 75$) |
| (10) | IR spectrum (KBr) Na salt 3300, 2950, 2925, 2875, 1710, 1560, 1450, 1400, 1375, 1330, 1320, 1295, 1250, 1240sh, 1220, 1210, 1175, 1155, 1135sh, 1110, 1075, 1040, 1020, 980, 960, 955, 925, 900, 875, 850, 830, 790 (broad), 765, 750, 720, 690, 660, 635, 610 (broad), 590, 560, 530 (broad), 480, 440, 425 (broad) $cm^{-1}$. |
| (11) | Mass spectrum (75 eV) m/e, (relative intensity) 756($M^+$)(8), 712(45), 697(3), 683(3), 669(10), 641(25), 603(7), 601(72), 572(19), 543(90), 514(72), 492(50), 474(15), 457(11), 447(15), 415(31), 393(40), 375(12), 368(15), 363(14), 349(95), 333(28), 331(30), 322(41), 310(45), 293(100), 275(75), 265(28), 250(55), 249(77), 240(20), 236(25), 225(23), 221(34), 209(44),, 207(46). |
| (12) | NMR spectrum (CDCl₃) 0.65, 0.72, 0.75, 0.80, 0.85, 0.88, 0.89, 0.91, 0.97, 1.05, 1.17, 1.25, 1.34, 1.42, 1.45, 1.47, 1.49, 1.60, 1.62, 1.70, 1.80, 1.86, 1.92, 1.98, 2.08, 2.34, 2.54, 2.64, 2.72, 2.85, |

-continued

(13) $^{13}$C-NMR spectrum (CDCl$_3$)
2.95, 2.97, 3.32, 3.42, 3.50, 3.60,
3.68, 3.78, 3.85, 3.88, 3.95, 3.98,
4.20, 4.30, 4.36, 4.42, 6.09 (δ)
213.79, 177.10, 125.64, 121.80,
105.04, 99.06, 88.45, 78.39,
71.11, 76.38, 75.83, 75.59,
74.73, 74.06, 71.56, 71.26,
68.52, 56.26, 49.56, 48.22, 41.02,
40.05, 38.77, 36.21, 33.10,
32.73, 31.94, 30.05, 29.68,
28.10, 26.57, 25.78, 22.67,
22.19, 20.05, 17.86, 16.64,
15.66, 14.38, 13.35, 13.16,
11.94, 11.21, 6.95, 6.52 (ppm)
(14) Toxicity: LD$_{50}$ = 51 mg/Kg (mice, orally).
(15) Antimicrobial spectra:

*The data in less than 200 of m/e are not included.

Minimum inhibitory concentration (mcg/ml) is shown in Table 1. In the Table, N indicates Nutrient agar medium, GN Glycerine nutrient medium and PS Potato-sucrose agar medium.

Table 1

| | | |
|---|---|---|
| Bacillus subtilis | N | 100 |
| Bacillus circulans | N | 12.5 |
| Bacillus megaterium | N | 50 |
| Staphylococcus aureus | N | 100 |
| Staphylococcus epidermidis | N | 50 |
| Micrococcus flavus | N | 100 |
| Micrococcus luteus | N | 100 |
| Mycobacterium smegmatis | GN | >100 |
| Mycobacterium phlei | GN | >100 |
| Mycobacterium avium | GN | >100 |
| Escherichia coli | N | >100 |
| Klebsiella pneumoniae | N | >100 |
| Proteus vulgaris | N | >100 |
| Psendomonas aeruginosa | N | >100 |
| Piricularia oryzae | PS | >100 |
| Alternaria kikuchiana | PS | >100 |

N: nutrient agar
GN: 4% glycerol nutrient agar
PS: potato-sucrose agar

The Streptomyces albus 80,614 has a long hypha which is not separated into bacillary or coccoid. The aerial mycelium of Streptomyces albus 80,614 is substantially straight and sometimes diverged to have sporephores having 2-3 turns in spiral form. The surface of the spore is smooth and has no spine and the shape of the spore is a long ellipsoid or cylindrical shape having 0.5-1.0μ × 1.0-1.5μ in size. The characteristics of Streptomyces albus 80,614 are as follows:

| Physiological reaction of Streptomyces albus 80,614 | |
|---|---|
| Test | Response |
| Milk coagulation | Negative |
| Milk peptonization | Negative |
| Melanin formation | Negative |
| Tyrosinase reaction | Negative |
| Nitrate reduction | Positive sometimes Negative |
| Starch hydrolysis | Positive |
| Liquefaction of gelation | Positive |
| Decomposition of cellulose | Negative |
| Chromogenicity | Negative |
| Oxygen requirement | Aerobic |
| Optimum growth conditions | pH 6.8 |
| | temperature 28° C |
| Range for growth | pH 5.5-8.2 |
| | temperature 21-37° C |

Utilization pattern of carbon sources by Streptomyces albus 80,614
(Pridham & Gottlieb's basal medium)

| | |
|---|---|
| ++: | glucose, fructose, galactose, mannitol, xylose, cellobiose mebibiose, inulin |
| +: | lactose, trehalose, starch |
| ±: | maltose, mannose, sucrose, salicin, arabinose |
| −: | melezitose, inositol, dulcitol, sorbitol, raffinose, adonitol, rhamnose |

++: good growth
+: fair growth
±: faint growth
−: no growth

Cultural characteristics of strain No. 80614

| Medium | Growth | Aerial mycelium | Soluble pigment |
|---|---|---|---|
| CZAPEK's agar | Good,raised,white to pale yellow | Poor,white | None |
| Starch inorganic salt agar | Poor or moderate, white to tan | Moderate, powdery, white to whitish gray | None |
| Glucose asparagine agar | Poor,thin,white to tan | Moderate to poor, velvety,white to whitish gray | None |
| Glycerine asparagine agar | Poor to moderate, tan | Poor to moderate, white | None |
| Calcium malate agar | Good,raised,white to pale tan | None or poor, white | None |
| Tyrosine agar | Poor,thin,white to pale brown | None | None or faint brown |
| Nutrient agar | Poor,thin,golden yellow | None or poor, white | None |
| Yeast malt extract agar | Good,yellowish brown | Good,white to yellowish white | Pale brown |
| Oatmeal agar | Poor,colorless | Poor to moderate, white to whitish gray | None or pale brown |
| Glucose nutrient agar | Poor,thin,yellowish white | None or poor, white | None |
| Glucose peptone agar | Poor,thin,yellowish white | None or poor, white | None or pale brown |
| Glycerol CZAPEK's agar | Good,raised,white to pale tan | Poor or none, white | None or pale brown |
| Potato plug | Poor,thin,brown | None or scanty, white to whitish gray | None |
| Cellulose | Scant,thin,colorless | None | None |
| Litmus milk | Ring growth in medium,colorless | None | Faint red |
| Egg | Poor,thin,yellowish white to white | None | None |
| LOEFFLER's serum medium | Good,raised, brownish yellow | None | None |

| Cultural characteristics of strain No. 80614 | | | |
|---|---|---|---|
| Medium | Growth | Aerial mycelium | Soluble pigment |
| (27° C 10 days) | | | |

Anticoccidal activity is an important property of SY-1 substance. For the prevention or treatment of coccidiosis in poultry, a non-toxic anticoccidal amount of SY-1 substance is administered to birds, preferably orally on a daily basis. SY-1 substance can be given in many ways, but it is most conveniently given with a physiologically acceptable carrier, preferably the feed. Although a variety of factors must be considered in determining an appropriate concentration of SY-1 substance, the rate of administration will be generally in the range of 0.003 to 0.06 percent by weight of unmedicated feed, and preferably in the range of 0.005 to 0.03 percent.

The ability to improve feed-utilization efficiency in animals is another important property of SY-1 substance. For example, SY-1 substance improves feed-utilization efficiency in ruminants when administered orally at rates of from about 0.05 mg/Kg/day to about 5.0 mg/Kg/day. Most beneficial results are achieved at rates of from about 0.1 mg/Kg/day to about 2.5 mg/Kg/day. A preferred method of administration of SY-1 bustance is by mixing it with the animals' feed, however, it can be administered in other ways, for example, tablets, drenches, boluses or capsuls.

EXAMPLE

*Streptomyces albus* 80614 (ATCC 21838) (FERM-P No.419) was inoculated in 100 liter of liquid medium consisting of 2% glucose, 1% starch, 4% corn steep liquor, 0.2% meat extract and 0.2% sodium chloride, in a 200 liter stainless steel tank at pH 7.0, and cultured at 30° C. for 120 hours in aerobic condition. Air was passed at the rate of 100 liter/min. and the medium stirred at the rate of 250 r.p.m. After culturing, whole fermentation broth was adjusted to pH 8 with NaOH, admixed with 2% by weight of diatomaceous earth and filtered. The filtrate was extracted twice with 50 liter of butyl acetate.

The mycelical mass was extracted twice with 30 liter of methanol, concentrated under vacuum, and further extracted twice with 10 liter of butyl acetate after evaporating off the methanol. Both ethyl acetate extracts were combined and concentrated under vacuum to 0.2 liter. The concentrate was extracted three times with 0.4 liter of n-hexane and concentrated under vacuum to 0.1 liter. The concentrate was applied to the column of 5 liter active almina charged with butyl acetate. The column was eluted with a mixture of ethyl acetate and methanol (50:1). Each fraction was checked by thin layer chromatography (developer: ethyl acetate, detector: 10% aqueous solution of surfuric acid) to identify SY-1 substance. Fractions containing single spot of SY-1 substance were combined and concentrated under vacuum.

The concentrated solution was allowed to stand in refrigerator (-5° C.) overnight for crystallization to occur. The crystals thus formed were separated by filtration and dried under vacuum to give 62.3 g of crude crystalline product. The crude crystals were dissolved in 800 ml of n-hexane, and concentrated under vacuum to 200 ml. Then a small amount of water was added to this solution, and the solution was allowed to stand in refrigerator overnight to crystallize crude SY-1 substance. The recrystallization was repeated twice to give 16.5 g of pure SY-1 substance Na salt. The product had the formula (I) wherein —COOH was converted to —COONa.

What is claimed is:

1. SY-1 substance having the formula

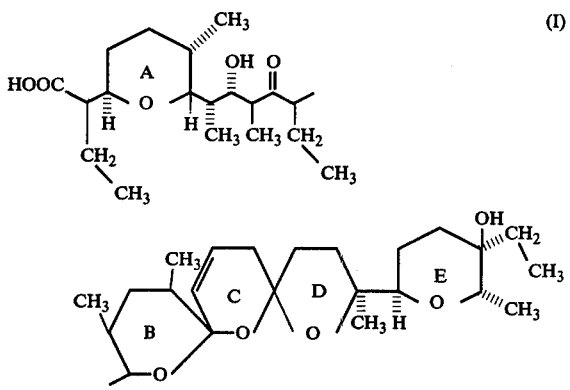

and pharmaceutically acceptable esters or salts thereof.

2. SY-1 substance having the formula (I) and esters or salts thereof according to claim 1 wherein the ester is a lower alkyl ester and the salt is an alkali metal salt or an alkaline earth metal salt.

3. An anticoccidal composition which comprises a poultry feed, containing an anticoccidal amount of from 0.003 to 0.06 percent by weight of said SY-1 substance of claim 1 based on the weight of the unmedicated portion of said feed.

4. A composition for improving feed utilization in animals containing as its principal active ingredient an effective amount of the SY-1 substance of claim 1 wherein said composition is a component of feed for ruminants, and said effective amount represents a dose of from 0.05 to 5.0 mg/kg/day per animal.

* * * * *